United States Patent
Balczewski et al.

(10) Patent No.: US 11,446,509 B2
(45) Date of Patent: Sep. 20, 2022

(54) CASE DRIVEN DESIGN FOR IMPLANTABLE MEDICAL DEVICE

(71) Applicant: Cardiac Pacemakers, Inc., St Paul, MN (US)

(72) Inventors: Ron A. Balczewski, Bloomington, MN (US); William J. Linder, Golden Valley, MN (US); Dan C. Goldman, North Oaks, MN (US); Nicholas J. Stessman, Minneapolis, MN (US); Aleksandra Kharam, Maple Grove, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 80 days.

(21) Appl. No.: 15/930,755

(22) Filed: May 13, 2020

(65) Prior Publication Data
US 2020/0360703 A1   Nov. 19, 2020

Related U.S. Application Data

(60) Provisional application No. 62/846,908, filed on May 13, 2019.

(51) Int. Cl.
*A61N 1/375* (2006.01)
*A61N 1/37* (2006.01)

(52) U.S. Cl.
CPC ......... *A61N 1/3756* (2013.01); *A61N 1/3758* (2013.01); *A61N 1/37512* (2017.08); *A61N 1/3702* (2013.01)

(58) Field of Classification Search
CPC ............... A61N 1/3756; A61N 1/3758; A61N 1/37512; A61N 1/3702
See application file for complete search history.

(56) References Cited

U.S. PATENT DOCUMENTS

| | | | |
|---|---|---|---|
| 2005/0197673 A1* | 9/2005 | Kroll | A61N 1/378 607/9 |
| 2006/0259098 A1* | 11/2006 | Erickson | A61N 1/3787 607/61 |
| 2007/0088394 A1* | 4/2007 | Jacobson | A61N 1/368 607/4 |
| 2013/0331910 A1* | 12/2013 | Lamont | A61N 1/3787 607/61 |
| 2018/0103908 A1* | 4/2018 | Balczewski | A61N 1/378 |

* cited by examiner

*Primary Examiner* — William J Levicky
(74) *Attorney, Agent, or Firm* — Faegre Drinker Biddle & Reath LLP

(57) ABSTRACT

A medical device includes: a case at least a portion of which functions as a first electrode; a second electrode disposed in a header coupled to the case; a core assembly, the core assembly including operational circuitry enclosed within a core assembly housing, wherein the case includes the core assembly housing; and a battery assembly, the battery assembly including a battery enclosed within a battery housing, where the case further comprises the battery housing; where the operational circuitry is configured to drive a regulated voltage onto the case.

20 Claims, 5 Drawing Sheets

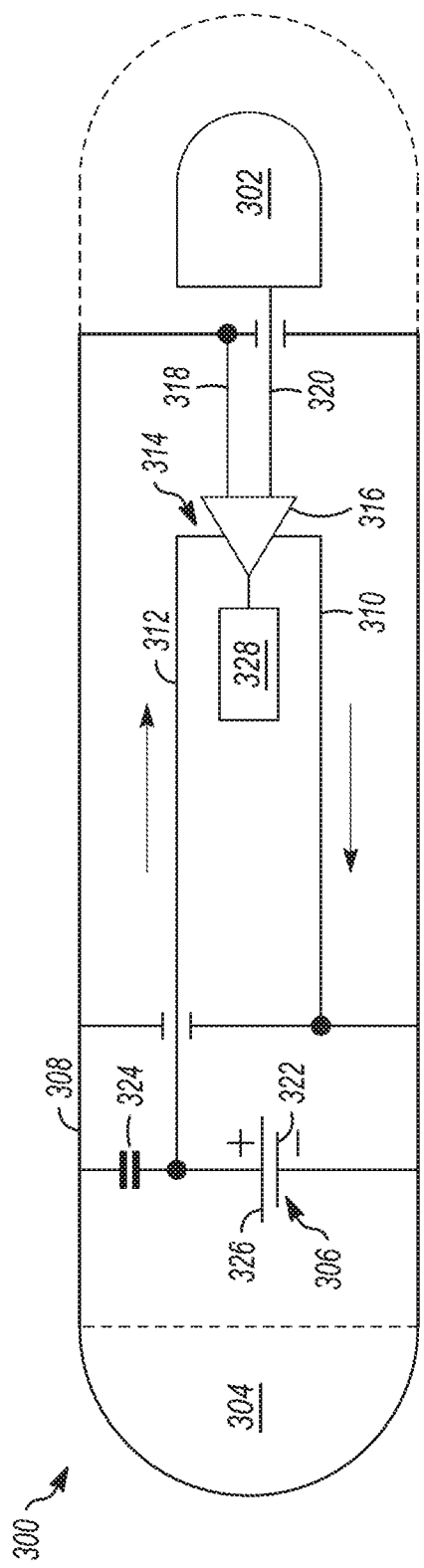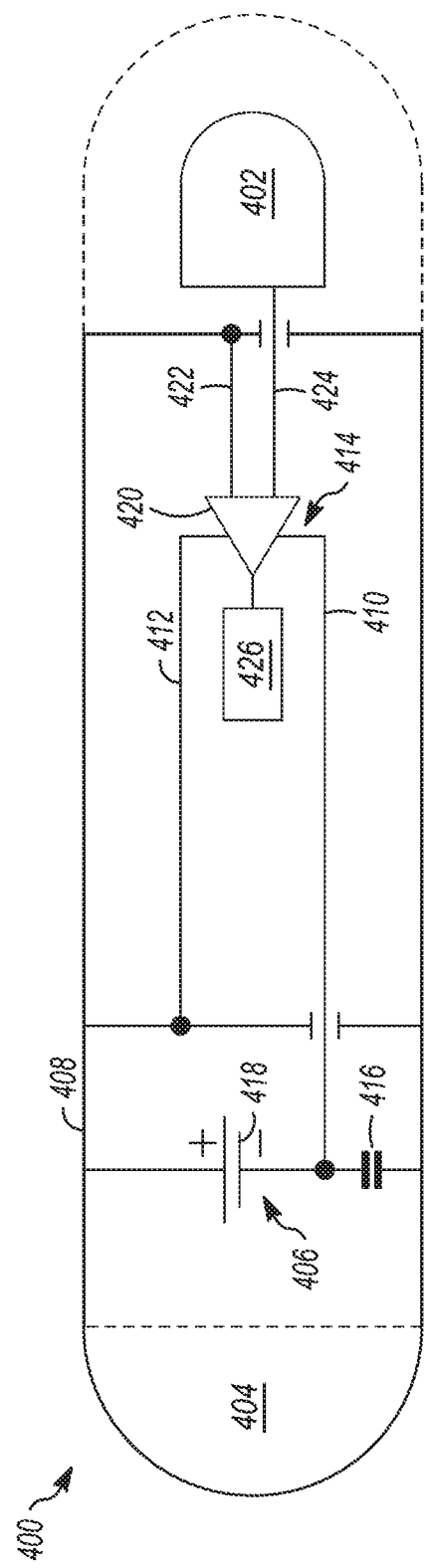

CASE DRIVEN DESIGN FOR IMPLANTABLE MEDICAL DEVICE

CROSS REFERENCE TO RELATED APPLICATION

This application claims priority to Provisional Application No. 62/846,908, filed May 13, 2019, which is herein incorporated by reference in its entirety.

TECHNICAL FIELD

Embodiments of the present disclosure relate to medical devices and systems for sensing physiological parameters. More specifically, embodiments of the disclosure relate to battery connection configurations of implantable medical devices.

BACKGROUND

Implantable medical devices (IMDs) may be configured to sense physiological parameters and/or provide therapy and may include one or more electrodes for performing aspects of these functions (e.g., sensing electrodes). The overall usable volume enclosed within a housing of an IMD may be adjusted based on considerations of patient comfort and performance. Examples of IMDs include implantable cardiac monitors (ICMs), implantable loop recorders (ILRs), and the like, which can be configured to be subcutaneously implanted in a patient for monitoring one or more physiological parameters such as, e.g., physiological parameters associated with the heart and/or the lungs.

To facilitate a more comfortable and efficient experience, these devices, which often are powered by an internal battery, may be designed to keep the overall volume of the device as small as possible. One way of reducing volume is to use the battery housing as part of the overall device case, as opposed to disposing the battery assembly (including the battery housing) within a device case. To further increase the efficient use of space in this type of device, one of the sensing electrodes may be electrically coupled to the battery housing and, in embodiments, the battery housing itself (or a portion thereof) may be used as the electrode.

SUMMARY

In an Example 1, a medical device comprising: a case, wherein at least a portion of the case functions as a first electrode; a second electrode disposed in a header coupled to the case; a core assembly, the core assembly comprising operational circuitry enclosed within a core assembly housing, wherein the case comprises the core assembly housing; and a battery assembly, the battery assembly comprising a battery enclosed within a battery housing, wherein the case further comprises the battery housing; wherein the operational circuitry is configured to drive a regulated voltage onto the case.

In an Example 2, the medical device of Example 1, the operational circuitry comprising a voltage regulator disposed between the battery and the case, the voltage regulator configured to drive the regulated voltage onto the case.

In an Example 3, the medical device of Example 2, wherein the voltage regulator is configured to produce the regulated voltage by reducing a power supply voltage provided by the battery.

In an Example 4, the medical device of either of Examples 1 or 2, further comprising a charge pump configured to facilitate increasing the regulated voltage to a voltage greater than a power supply voltage provided by the battery.

In an Example 5, the medical device of any of Examples 2-4, wherein the first and second electrodes are coupled to an input component, and wherein the voltage regulator is configured to provide a power supply to the input component.

In an Example 6, the medical device of any of Examples 2-4, wherein the first and second electrodes are coupled to an input component, and further comprising an additional voltage regulator, wherein the additional voltage regulator is configured to provide a power supply to the input component.

In an Example 7, the medical device of any of Examples 1-6, wherein operational circuitry is configured to drive the regulated voltage onto the case in response to determining that the device is in an active mode.

In an Example 8, the medical device of any of Examples 1-7, wherein the operational circuitry is configured to drive the regulated voltage at a level that is selected based on a battery discharge state.

In an Example 9, the medical device of any of Examples 1-8, wherein the regulated voltage is positive.

In an Example 10, a method of manufacturing a medical device comprising: providing a case, wherein at least a portion of the case functions as a first electrode; couple a header to the case; dispose a second electrode in the header; provide a core assembly, the core assembly comprising operational circuitry enclosed within a core assembly housing, wherein the case comprises the core assembly housing; and couple a battery assembly to the core assembly, the battery assembly comprising a battery enclosed within a battery housing, wherein the case further comprises the battery housing; wherein the operational circuitry is configured to drive a regulated voltage onto the case.

In an example 11, the method of Example 10, further comprising providing a voltage regulator disposed between the battery and the case, the voltage regulator configured to drive the regulated voltage onto the case.

In an Example 12, the method of Example 11, wherein the voltage regulator is configured to produce the regulated voltage by reducing a power supply voltage provided by the battery.

In an Example 13, the method of any of Examples 2-4, further comprising coupling the first and second electrodes to an input component, and wherein the voltage regulator is configured to provide a power supply to the input component.

In an Example 14, the method of any of Examples 2-4, further comprising coupling the first and second electrodes to an input component, and further comprising providing an additional voltage regulator, wherein the additional voltage regulator is configured to provide a power supply to the input component.

In an Example 15, the method of any of Examples 10-14, wherein operational circuitry is configured to drive the regulated voltage onto the case in response to determining that the device is in an active mode method of any of claims 10-14, wherein operational circuitry is configured to drive the regulated voltage onto the case in response to determining that the device is in an active mode.

In an Example 16, a medical device comprising: a case, wherein at least a portion of the case functions as a first electrode; a second electrode disposed in a header coupled to the case; a core assembly, the core assembly comprising operational circuitry enclosed within a core assembly housing, wherein the case comprises the core assembly housing;

and a battery assembly, the battery assembly comprising a battery enclosed within a battery housing, wherein the case further comprises the battery housing; wherein the operational circuitry is configured to drive a regulated voltage onto the case.

In an Example 17, medical device of Example 16, the operational circuitry comprising a voltage regulator disposed between the battery and the case, the voltage regulator configured to drive the regulated voltage onto the case.

In an Example 18, medical device of Example 17, wherein the voltage regulator is configured to produce the regulated voltage by reducing a power supply voltage provided by the battery.

In an Example 19, the medical device of Example 16, further comprising a charge pump configured to facilitate increasing the regulated voltage to a voltage greater than a power supply voltage provided by the battery.

In an Example 20, the medical device of Example 17, wherein the first and second electrodes are coupled to an input component, and wherein the voltage regulator is configured to provide a power supply to the input component.

In an Example 21, the medical device of Example 17, wherein the first and second electrodes are coupled to an input component, and further comprising an additional voltage regulator, wherein the additional voltage regulator is configured to provide a power supply to the input component.

In an Example 22, the medical device of Example 16, wherein operational circuitry is configured to drive the regulated voltage onto the case in response to determining that the device is in an active mode.

In an Example 23, the medical device of Example 17, wherein the operational circuitry is configured to drive the regulated voltage at a level that is selected based on a battery discharge state.

In an Example 24, the medical device of Example 16, wherein the regulated voltage is positive.

In an Example 25, a method of manufacturing a medical device comprising: providing a case, wherein at least a portion of the case functions as a first electrode; couple a header to the case; dispose a second electrode in the header; provide a core assembly, the core assembly comprising operational circuitry enclosed within a core assembly housing, wherein the case comprises the core assembly housing; and couple a battery assembly to the core assembly, the battery assembly comprising a battery enclosed within a battery housing, wherein the case further comprises the battery housing; wherein the operational circuitry is configured to drive a regulated voltage onto the case.

In an Example 26, the method of Example 25, further comprising providing a voltage regulator disposed between the battery and the case, the voltage regulator configured to drive the regulated voltage onto the case.

In an Example 27, the method of Example 26, wherein the voltage regulator is configured to produce the regulated voltage by reducing a power supply voltage provided by the battery.

In an Example 28, the method of Example 25, further comprising coupling the first and second electrodes to an input component, and wherein the voltage regulator is configured to provide a power supply to the input component.

In an Example 29, the method of Example 26, further comprising coupling the first and second electrodes to an input component, and further comprising providing an additional voltage regulator, wherein the additional voltage regulator is configured to provide a power supply to the input component.

In an Example 30, the method of Example 15, wherein operational circuitry is configured to drive the regulated voltage onto the case in response to determining that the device is in an active mode.

In an Example 31, a medical device comprising: a case, wherein at least a portion of the case functions as a first electrode; a second electrode disposed in a header coupled to the case; a core assembly, the core assembly comprising operational circuitry enclosed within a core assembly housing, wherein the case comprises the core assembly housing; and a battery assembly, the battery assembly comprising a battery enclosed within a battery housing, wherein the case further comprises the battery housing; wherein the operational circuitry comprises a voltage regulator that is configured to drive the regulated voltage onto the case.

In an Example 32, medical device of Example 31, wherein the voltage regulator is configured to produce the regulated voltage by reducing a power supply voltage provided by the battery.

In an Example 33, the medical device of Example 31, further comprising a charge pump configured to facilitate increasing the regulated voltage to a voltage greater than a power supply voltage provided by the battery.

In an Example 34, the medical device of Example 31, wherein the first and second electrodes are coupled to an input component, and wherein the voltage regulator is configured to provide a power supply to the input component.

In an Example 35 the medical device of Example 31, wherein the first and second electrodes are coupled to an input component, and further comprising an additional voltage regulator, wherein the additional voltage regulator is configured to provide a power supply to the input component.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 3 depicts a conceptual circuit diagram depicting an illustrative circuit for an IMD, in accordance with the prior art.

FIG. 4 depicts a conceptual circuit diagram depicting an illustrative circuit for an IMD, in accordance with the embodiments of the disclosure.

Figure 1:
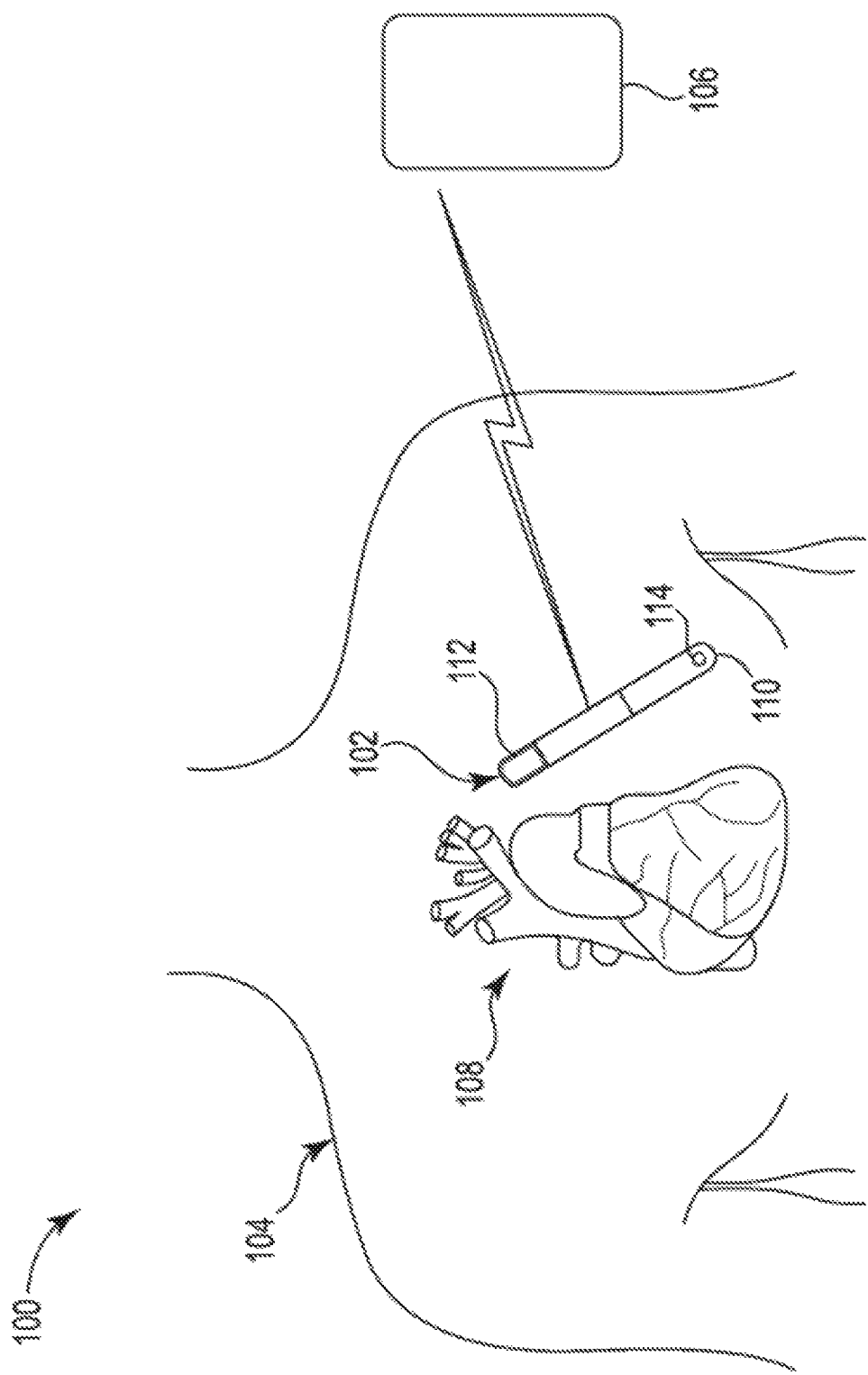
FIG. 1 is a schematic illustration depicting a patient monitoring system, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the disclosure include an implantable medical device (IMD) in which a portion of the operational circuitry of the device is electrically coupled to the case of the IMD such that a sensing component senses signals between the case (housing) and an electrode disposed in the header of the device. In some previous devices, this was accomplished by using a case-negative design—that is, by shorting an anode terminal of the power circuitry to the case, which resulted in electrochemical issues such as, for example chemical reactions that caused cracking.

To address the electrochemical issues, alternative solutions have included using a case-positive design. In the case-positive design, the case is shorted to the positive battery terminal. This case-positive design appeared to resolve the electrochemical issue but caused injection of a battery voltage ripple as a common mode noise that needed to be rejected by the sense filter. Rejection of this type and/or amount of noise, using a filter, may be challenging and, as such, may result in diminished accuracy in sensing.

Embodiments of the subject matter disclosed herein are directed to a case-driven solution in which a positive voltage is driven onto the case. The inventors have found that driving a voltage onto the case may resolve the electrochemical issues, while reducing the common mode noise that is to be rejected by the sense filter. According to embodiments, the driven voltage may be selected, for example, to be sufficient to stop electrochemical processes such as AEC and to have enough bypass capacitance to keep ripple due to capacitance between the battery and the case at or below a specified level. According to embodiments, the voltage may be driven onto the case throughout the device's operating life, during specific time periods only, and/or the like.

FIG. 1 is a schematic illustration of a system 100 including an IMD 102 implanted within a patient's body 104 and configured to communicate with a receiving device 106. In embodiments, the IMD 102 may be configured to be implanted subcutaneously within an implantation location or pocket in the patient's chest or abdomen and may be configured to monitor (e.g., sense and/or record) physiological parameters associated with the patient's heart 108. The IMD 102 may be an implantable cardiac monitor (ICM) (e.g., an implantable diagnostic monitor (IDM), an implantable loop recorder (ILR), etc.) configured to record physiological parameters such as, for example, electrical signals (e.g., electrocardiograms), one or more cardiac activation signals, heart sounds, blood pressure measurements, oxygen saturations, and/or the like. The IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. Such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations. For example, in embodiments, the IMD 102 may be configured to facilitate cardiac rhythm diagnostics, e.g., by monitoring heart rate, arrhythmias, and/or the like.

For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient. In embodiments, however, the IMD 102 may include any type of IMD, any number of different components of an implantable system, and/or the like having a housing and being configured to be implanted in a patient's body 104. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the patient's body and/or the IMD 102. In various embodiments, the IMD 102 may include both defibrillation and pacing/CRT capabilities (e.g., a CRT-D device).

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102.

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2A:
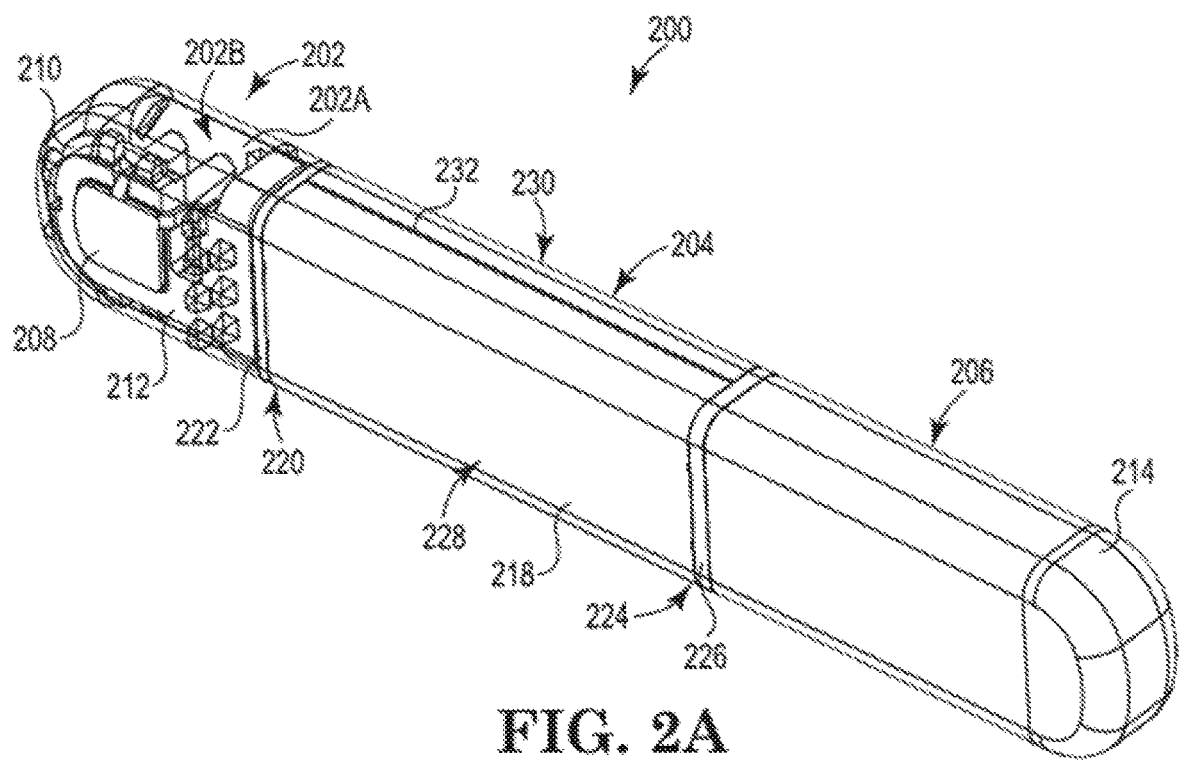
FIG. 2A is a perspective view of an implantable medical device (IMD), in accordance with embodiments of the disclosure.

FIG. 2A is a perspective view of an implantable medical device (IMD) 200, in accordance with embodiments of the disclosure. The IMD 200 may be, or may be similar to, the IMD 102 depicted in FIG. 1. As shown, the IMD 200 includes a hermetically sealed case, and may include a header 202 arranged at or near a first end 220 of a core assembly 204. A battery assembly 206 (which may include one or more batteries) is arranged near a second end 224 of the core assembly 204. The header 202 includes a header housing 202A that encloses an interior region 202B. The header 202 may house various circuitry components within its interior, which may include a portion of the operational circuitry of the IMD 200. The header housing 202A may contact a patient's bodily tissue when the IMD 200 is subcutaneously implanted in an implantation location or pocket in the patient's chest or abdomen. The interior region 202B of the header 202 may house circuit components (e.g., an electrode 208 and an antenna 210) positioned and supported by a scaffold assembly 212. As shown, the IMD 200 may include, in addition to the electrode 208, an electrode 214 electrically and/or physically coupled to the battery assembly 206. In embodiments, the electrode 214 may be integrated with the battery assembly 206, a housing of the battery assembly 206, and/or the like. That is, for example, in embodiments, the electrode 214 may be the battery assembly housing, which may also be referred to as a "case." In order to enable sensing of physiological parameters within the patient, the electrode 208 may be positioned to be flush with an interior surface of the housing 202A of the header 202. In other instances, the electrode 208 may be positioned by the scaffold assembly 212 to form a portion of an exterior surface of the housing 202A of the header 202.

Figure 2B:
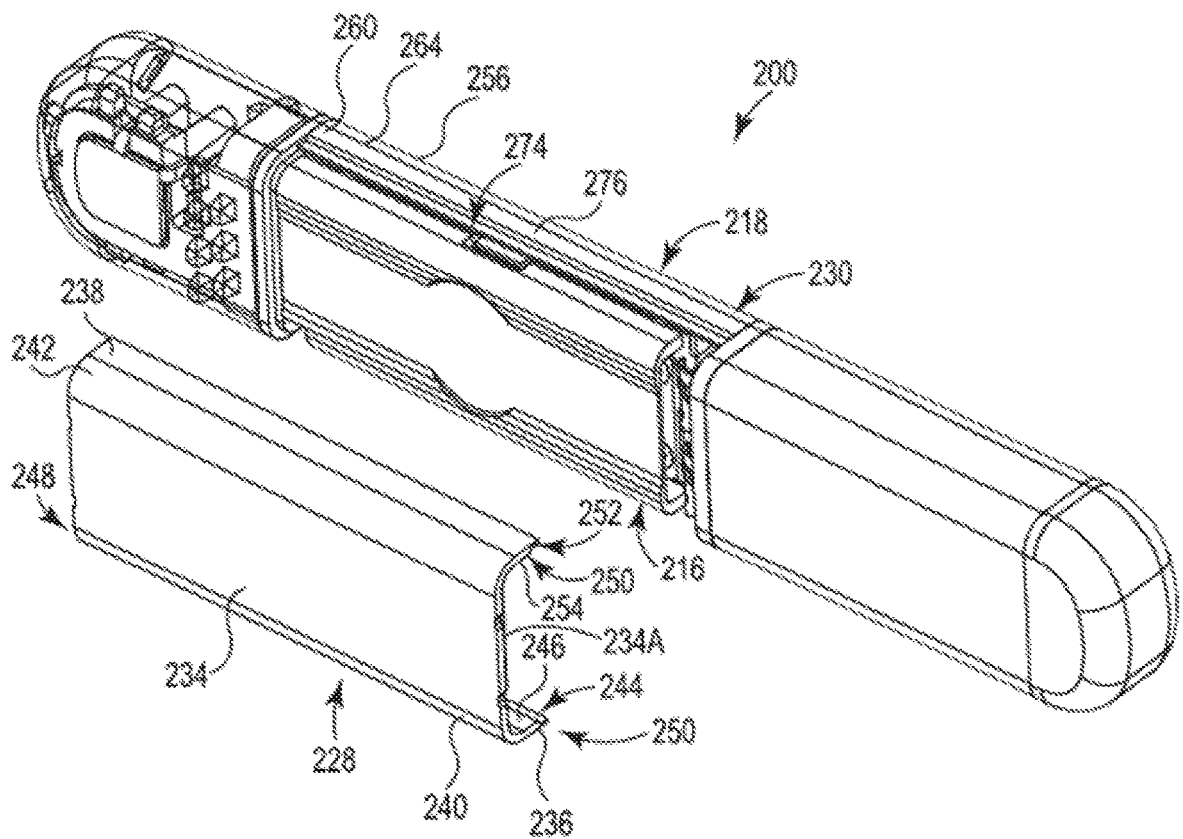
FIGS. 2B and 2C are partially-exploded perspective views of the IMD depicted in FIG. 2A, in accordance with embodiments of the disclosure.

As shown in FIG. 2B, the core assembly 204 includes a core circuitry assembly 216 enclosed within a core assembly housing 218. In embodiments, the core assembly housing 218 may be physically and/or electrically coupled to and/or integrated with the battery housing 206A, in which case the combination of the core assembly housing 218 and the battery housing 206A may be referred to as a "case." The core circuitry assembly 216 includes operational circuitry configured to perform one or more various functions described herein and may include processing circuitry, input circuitry, output circuitry, communication circuitry, and/or the like. Circuitry may include any number of different types of electrical and/or logical connections, components, and/or the like, and may include, for example, conductive elements (e.g., wires, conductive traces, etc.), processors (e.g., microprocessors, virtual processors, etc.), and/or other electrical and/or logical components. Thus, circuitry may include hardware, firmware, and/or software. The core assembly housing 218 is coupled, at the first end 220, to a first feed-through assembly 222, and coupled, at the second end 224, to a second feed-through assembly 226. The feed-through assembly 222 may be configured to provide a throughput for connections configured to connect the circuitry components of the header 202 (e.g., the electrode 208 and the antenna 210) to the core circuitry assembly 216. Similarly, the feed-through assembly 226 may be configured to provide a throughput for connections configured to connect one or more batteries (e.g., which are a part of the battery assembly 206) and/or the electrode 214 to the core circuitry assembly 216. In embodiments, the combination of the header housing, core assembly housing, battery housing, and feedthrough assembly surface form the case 201.

As illustrated in FIG. 2A, the core assembly housing 204 includes a first portion 228 configured to be coupled to a second portion 230 along a weld seam 232. The first portion 228 and second portion 230 may be coupled together by laser welding, seam welding, and/or the like. As shown, for example, in FIGS. 2B and 2C, the first portion 228 of the core assembly housing 218 includes a side wall 234, a lower wall 236, and an upper wall 238. The lower wall 236 and the upper wall 238 each extend, perpendicularly (or at least approximately perpendicularly) in a direction away from an inside surface 234A of the side wall 234. As shown, the lower wall 236 is coupled to the side wall 234 by a curved corner portion 240, and the upper wall 238 is coupled to the side wall 234 by a curved corner portion 242. In embodiments, the curved corner portions 240 and 242 may be integrated with the lower and upper walls 236 and 238, respectively, the side wall 234, and/or the like. That is, for example, the first portion 228 may be a single piece of metal, formed in a press or a mold. In embodiments, the curved corner portions 240 and 242 may be separate components. The curved corner portions 240 and 242 each may be designed to have any desirable radius of curvature. For example, the curved corner portions 240 and 242 each may be configured to have a radius of curvature that provides a desired amount of volume enclosed within the core assembly housing 218.

Figure 2C:
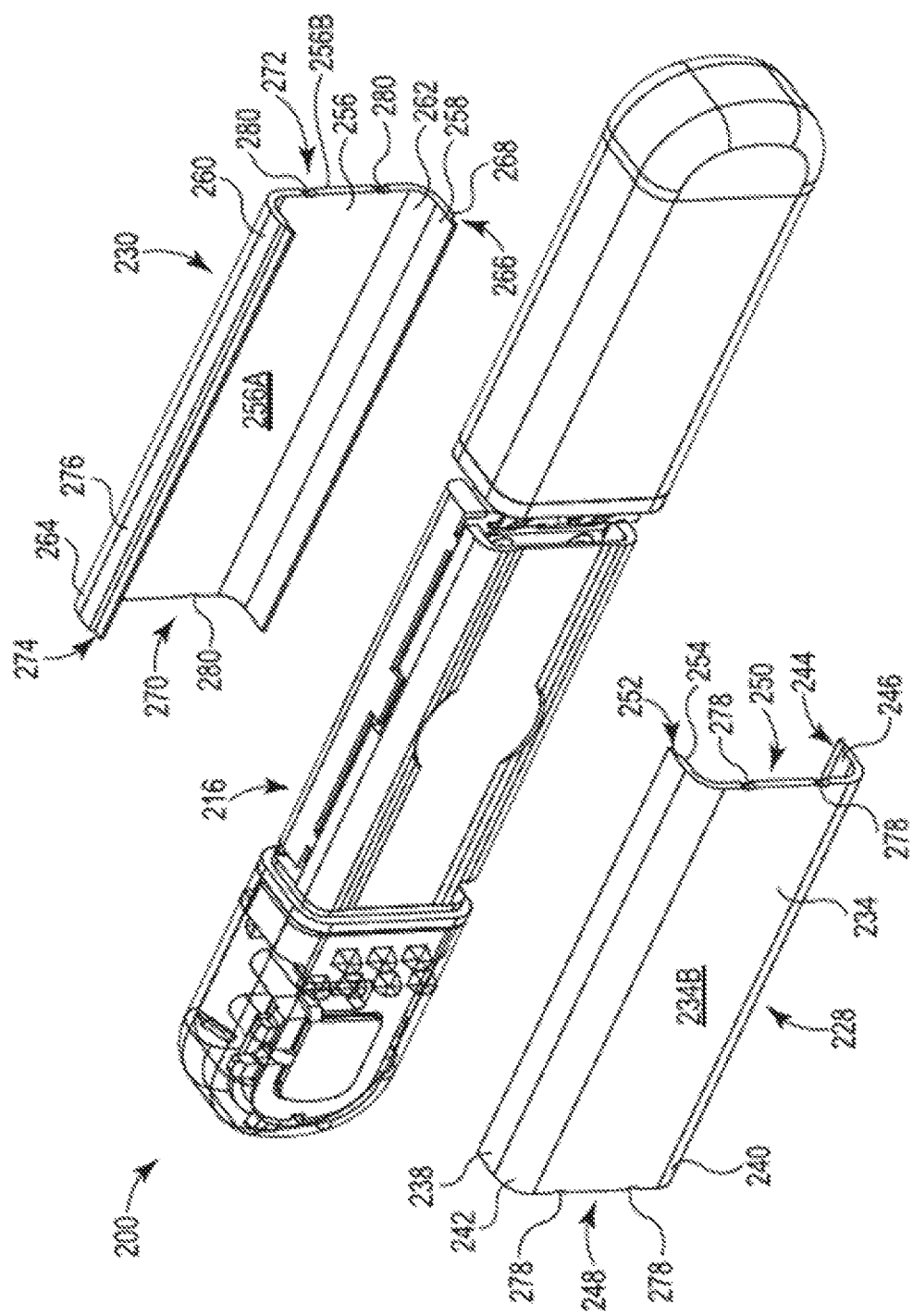

As illustrated, for example, in FIGS. 2B and 2C, the lower wall 236 includes a flange 244 that is recessed with respect to an inside surface 246 of the lower wall 236, and that extends from a first end 248 of the first portion 228 to a second end 250 thereof. The flange 244 may be a thinned portion of the lower wall 236. In embodiments, the flange 244 may be welded to the lower wall 236. Similarly, the upper wall 238 includes a flange 252 that is recessed with respect to an inside surface 254 of the upper wall 238, and that extends from the first end 248 of the first portion 228 to the second end 250 thereof. The flange 252 may be a thinned portion of the upper wall 238. In embodiments, the flange 252 may be welded to the upper wall 238.

As is also shown, for example, in FIGS. 2B and 2C, the second portion 230 of the core assembly housing 218 includes a side wall 256, a lower wall 258, and an upper wall 260. The lower wall 258 and the upper wall 260 each extend, perpendicularly (or at least approximately perpendicularly) in a direction away from an inside surface 256A of the side wall 256. As shown, the lower wall 258 is coupled to the side wall 256 by a curved corner portion 262, and the upper wall 260 is coupled to the side wall 256 by a curved corner portion 264. In embodiments, the curved corner portions 262 and 264 may be integrated with the lower and upper walls 258 and 260, respectively, the side wall 256, and/or the like. That is, for example, the second portion 230 may be a single piece of metal, formed in a press or a mold. In embodiments, the curved corner portions 262 and 264 may be separate components. The curved corner portions 262 and 264 each may be designed to have any desirable radius of curvature such as, for example, a radius of curvature that is identical or similar to the radius of curvature of each of the curved corner portions 240 and 242. For example, the curved corner portions 262 and 264 each may be configured to have a radius of curvature that provides a desired amount of volume enclosed within the core assembly housing 218.

As illustrated, for example, in FIGS. 2B and 2C, the lower wall 258 includes a flange 266 that is recessed with respect to an outside surface 268 of the lower wall 258, and that extends from a first end 270 of the second portion 230 to a second end 272 thereof. The flange 266 may be a thinned portion of the lower wall 258. In embodiments, the flange 266 may be welded to the lower wall 258. Similarly, the upper wall 260 includes a flange 274 that is recessed with respect to an outside surface 276 of the upper wall 260, and that extends from the first end 270 of the second portion 230 to the second end 272 thereof. The flange 274 may be a thinned portion of the upper wall 260. In embodiments, the flange 274 may be welded to the upper wall 260.

The core assembly housing 218 may also include notches 278 defined in the first and second ends 248 and 250, respectively, of the first portion 228, and extending from the inside surface 234A to the outside surface 234B of the side wall 234. Similarly, the core assembly housing 218 may also include notches 280 defined in the first and second ends 270 and 272, respectively, of the second portion 230, and extending from the inside surface 256A to the outside surface 256B of the side wall 256. The notches 278 and 280 may be an artifact of a progressive die manufacturing process in which the first and second portions 228 and 230 of the core assembly housing 218 are produced in a continuous strip and formed into shape in successive operations. The notches 278 and 280 may be left when the first and second portions 228 and 230 are broken away from the strip. In embodiments, the strip may be configured such that the notches are small enough to be consumed in the weld pool when the core assembly housing 218 is welded to the first and second feedthrough assemblies 222 and 226. For example, in embodiments, the notches 278 and 280 may extend into the portions 228 and 230 by less than or equal to approximately 0.003 inches.

The illustrative IMD 200 shown in FIGS. 2A-2C is not intended to suggest any limitation as to the scope of use or functionality of embodiments of the subject matter disclosed throughout this disclosure. Neither should the illustrative IMD 200 be interpreted as having any dependency or requirement related to any single component, feature, or combination of components or features illustrated in FIGS. 2A-2C. For example, in embodiments, the illustrative IMD 200 may include different and/or additional components and/or features. Any number of other components, features, or combinations of components or features can be integrated with the illustrative IMD 200 depicted in FIGS. 2A-2C, all of which are considered to be within the ambit of this disclosure. Additionally, any one or more of the components and/or features depicted in FIGS. 2A-2C can be, in embodiments, integrated with various ones of the other components and/or features depicted therein (and/or components and/or features not illustrated).

Moreover, as used herein, the terms "side wall," "lower wall," "upper wall," "upward," and "downward" are used to refer to the specific features to which they refer, but are characterized in the context of the illustrations for clarity and to describe relative orientations of features with respect to other features, and are not intended to imply any particular orientation of the IMD 200, or absolute (or preferred) orientations of features thereof. That is, for example, even if the IMD 200 were to be rotated around a longitudinal axis such that the outer surface 234B of the side wall 234 was parallel to a horizontal plane, the side wall 234 would still be referred to, for the purposes of this disclosure, as a "side wall."

FIG. 3 is a functional schematic diagram of circuitry 300 associated with an IMD, according to a case-negative design, in accordance with the prior art. The circuitry 300 depicted in FIG. 3 may be associated with the sensing of physiological signals by two electrodes 302 and 304. The circuitry 300 includes a battery 306 that is enclosed within a case 308, to which the electrode 304 is electrically coupled. In embodiments, the case 308 (or a portion thereof) may function as the electrode 304. Supply rails 310 and 312 define the current path for delivery of energy to operational circuitry 314, and are electrically coupled to the battery 306.

In operation, the electrodes 302 and 304 obtain a physiological signal from a patient, and transmit that obtained physiological signal to an input component 316 (e.g., a sense amplifier). As shown in FIG. 3, the electrode 304 is directly coupled to a first input node of the input component 316 via a conductive element 318 (e.g., one or more conductive traces and/or wires), while the electrode 302 is directly coupled, via a conductive element 320 (e.g., one or more conductive traces and/or wires), to a second input node of the input component 316.

According to embodiments, the conductive element 318 is directly coupled to the negative (or, in embodiments, positive) terminal 322 (anode) of the battery 306, and to the common (ground) reference (not shown) of the operational circuitry 314. In embodiments, the ground reference may be used as a Kelvin Connection, joining the battery to the sensing electrode 304. As shown, a capacitance (e.g., caused by the battery electrolyte coupling to the battery case) 324 may be disposed between the positive terminal 326 and the case 308. As is further depicted in FIG. 3, the output node of the input component 316 is coupled to processing circuitry 328. The processing circuitry 328 may include any number of different types of processing components, including, for example, one or more microprocessors, circuit components, and/or the like. In the case-negative design depicted in FIG. 3, the case 308 is shorted to the negative battery terminal 322. In embodiments, doing so removes battery noise from sensed signals, but creates electrochemical issues that may cause damage to the case 308, the battery 306, and/or other components of the IMD 300.

FIG. 4 is a functional schematic diagram of circuitry 400 associated with an IMD, employing a case-positive design, in accordance with the subject matter disclosed herein. The circuitry 400 depicted in FIG. 4 may be associated with the sensing of physiological signals by two electrodes 402 and 404. The circuitry 400 includes a battery 406 that is enclosed within a case 408, to which the electrode 404 is electrically coupled. In embodiments, the case 408 (or a portion thereof) may function as the electrode 404. Supply rails 410 and 412 define the current path for delivery of energy to operational circuitry 414 and are electrically coupled to the battery 406.

Supply rails 410 and 412 define the current path for delivery of energy to operational circuitry 414. The positive supply rail 412 is electrically coupled to the battery 406 through the case 408 (or a portion thereof), and the negative supply rail 410 is electrically coupled directly to the battery 406. As shown, a capacitance 416 may be disposed between the negative terminal 418 and the case 408. In operation, the electrodes 402 and 404 obtain a physiological signal from a patient, and transmit that obtained physiological signal to an input component 420 (e.g., a sense amplifier). As shown in FIG. 4, the electrode 404 is directly coupled to a first input node of the input component 420 via the case 408 and a conductive element 422, while the electrode 402 is directly coupled, via a conductive element 424 (e.g., one or more conductive traces and/or wires), to a second input node of the input component 420. As is further depicted in FIG. 4, the output node of the input component 420 is coupled to processing circuitry 426.

As can be seen from inspection of FIGS. 3 and 4, the circuit configuration depicted in FIG. 4 may be similar to the circuit configuration depicted in FIG. 3, with the exception of the configuration of the components that short a battery terminal to the case. In the case-negative design of FIG. 3, the case is shorted to the negative battery terminal, while, in the case-positive design of FIG. 4, the case is shorted to the positive battery terminal. In the case-positive design, the electrochemical issues of the case-negative design are resolved, but a battery voltage ripple is injected as a common mode noise. Rejecting this noise with the sense filter can be challenging. For example, voltage ripple from the battery may be superimposed on a sense signal sensed between the can and the header electrode, and may be tens of thousands of times the magnitude of the sense signal, which may be only several hundred microvolts.

The illustrative circuitry 400 shown in FIG. 4 is not intended to suggest any limitation as to the scope of use or functionality of embodiments of the subject matter disclosed throughout this disclosure. Neither should the illustrative circuitry 400 be interpreted as having any dependency or requirement related to any single component, feature, or combination of components or features illustrated in FIG. 4. For example, in embodiments, the illustrative circuitry 400 may include different and/or additional components and/or features. Any number of other components, features, or combinations of components or features can be integrated with the illustrative circuitry 400 depicted in FIG. 4, all of which are considered to be within the ambit of this disclosure. Additionally, any one or more of the components and/or features depicted in FIG. 4 can be, in embodiments, integrated with various ones of the other components and/or features depicted therein (and/or components and/or features not illustrated).

Figure 5:
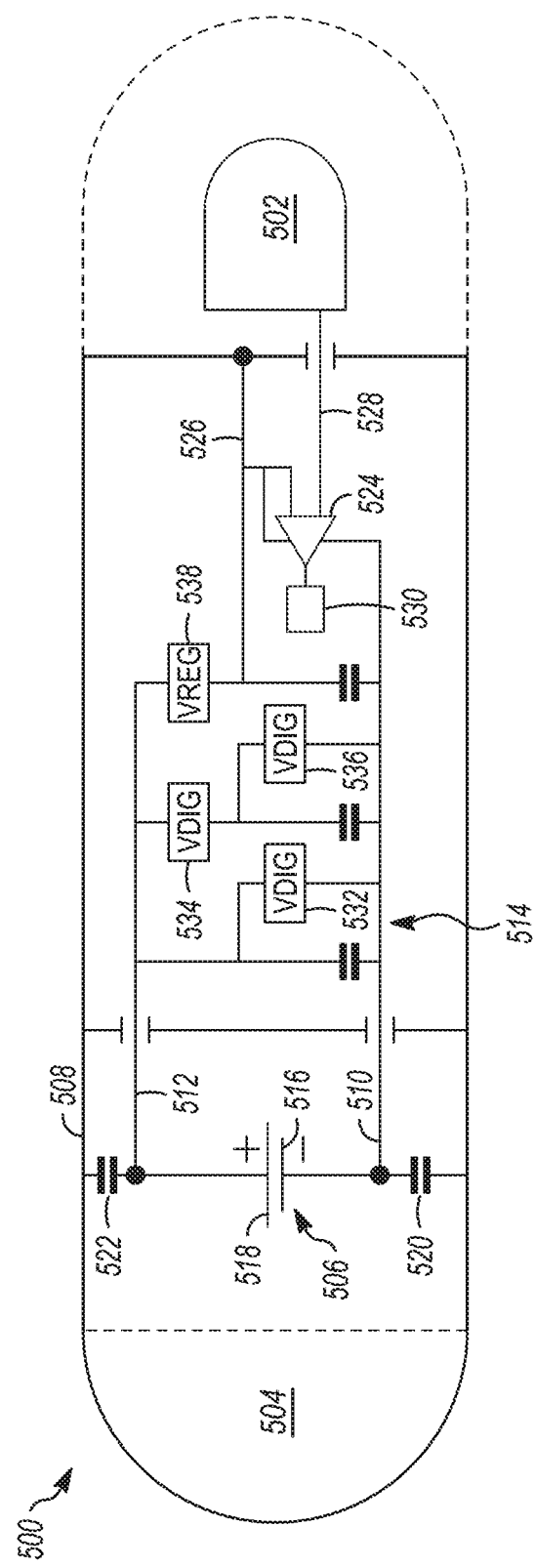
FIG. 5 depicts a conceptual circuit diagram depicting an illustrative circuit for an IMD, in accordance with embodiments of the disclosure.

FIG. 5 is a functional schematic diagram of circuitry 500 associated with an IMD, employing a case-driven design, in accordance with the subject matter disclosed herein. The IMD may be, include, or be included in, the IMD 102 depicted in FIG. 1 and/or the IMD 200 depicted in FIGS. 2A-2C. According to embodiments, in the case-driven design, a regulated voltage is driven to the case. This design may facilitate mitigating the electrochemical issues of the case-negative design, while avoiding the challenging common mode noise of the case-positive design.

The circuitry 500 depicted in FIG. 5 may be associated with the sensing of physiological signals by two electrodes 502 and 504. The circuitry 500 includes a battery 506 that is enclosed within a case 508, to which the electrode 504 is electrically coupled. In embodiments, the case 508 (or a portion thereof) may function as the electrode 504. Supply rails 510 and 512 define the current path for delivery of energy to operational circuitry 514 and are electrically coupled to the battery 506.

Supply rails 510 and 512 define the current path for delivery of energy to operational circuitry 514. As shown, the negative battery terminal 516 and the positive battery terminal 518 are isolated from the case 508 by a respective capacitance 520, 522. The positive supply rail 512 is electrically coupled directly to the battery 506 and the negative supply rail 510 is electrically coupled directly to the battery 506. In operation, the electrodes 502 and 504 obtain a physiological signal from a patient, and transmit that obtained physiological signal to an input component 524 (e.g., a sense amplifier). As shown in FIG. 5, the electrode 504 is directly coupled to a first input node of the input component 524 via the case 508 and a conductive element 526, while the electrode 502 is directly coupled, via a conductive element 528 (e.g., one or more conductive traces and/or wires), to a second input node of the input component 524. As is further depicted in FIG. 4, the output node of the input component 524 is coupled to processing circuitry 530.

As shown in FIG. 5, the operating circuitry 514 includes a number of different components such as, for example, a radio frequency (RF) component 532, a digital processing component 536 (DIG), a DIG voltage regulator (VDIG) 534, and a driving voltage regulator (VREG) 538. In embodiments, the functions of the RF component 532, the DIG 534, and the VDIG 536 are not germane to the present disclosure, but are illustrated as examples of various types of operational components might be present in some implementations of embodiments of the subject matter disclosed herein.

According to embodiments, the driving voltage regulator (VREG) 538 may be configured to drive a voltage onto the can 508. In embodiments, VREG 538 may be a voltage regulator circuit component, a number of voltage regulator circuit components, a processor, logic, and/or the like. VREG 538 may, as illustrated in FIG. 5, also be configured to drive the power supply for the input component 524 (e.g., sense amp). Using a common power source to drive the case and to power the sense circuit may also improve the sense circuit common mode rejection ratio. Even though the case is being driven there will still be some voltage ripple on the case from the battery. This voltage ripple will be a common mode noise signal that the sense circuit needs to reject. When the same voltage source is used to power the sense filters and drive the case some factors affecting common mode rejection such as transistor body capacitance can be canceled out. According to embodiments, the circuit power path can be common (coupled) with the circuit input from the case if the common net impedance is kept small enough to prevent voltage noise (due to current x impedance) from exceeding the desired noise floor for the system.

In other embodiments, a separate voltage regulator may be provided for driving the sense amp. In the embodiments illustrated in FIG. 5, the driven voltage is generated by regulating down a voltage from the battery 506, generating a quieter voltage that is configured to mitigate or stop the electrochemical issues, while having enough bypass capacitance or drive strength to mitigate ripple due to capacitance between the battery 506 and the case 508.

In embodiments, for example, the driven voltage may be configured to be approximately the same as the power supply for the sense circuit. That is, for example, the driven voltage may be selected to be approximately equal to the positive power supply. In embodiments, for example, the voltage on the positive side of the circuitry 500 may be approximately 3 V, and the driven voltage may be between approximately 1 and 2.5 V (e.g., 1 V, 2.2 V, etc.). In embodiments, the driven voltage may be selected to be large enough for producing a signal that is sufficient for mitigating the electrochemical reaction while producing a reliable and accurate sense signal. In embodiments, for example, the VREG 326 may be configured to be within 7/10 of a volt of the positive power supply. According to embodiments, VREG 538 may include any number of circuit components and may be configured to generate a power supply for the can 508 that, from an AC loading perspective, follows the negative terminal battery voltage. In embodiments, the driven voltage may be higher than the positive battery terminal using an amplifying circuit such as a charge pump. This may be desirable for biasing certain circuit inputs at a higher voltage In contrast, for example, to the case-positive design depicted in FIG. 4, in which the sense amp does all of the work in rejecting the noise, in the case-driven design depicted in FIG. 5, VREG 538 does most of the work.

According to embodiments, the case-driven design may be implemented for driving a voltage on to a case according to any number of different schedules, arrangements, and/or the like. For example, in embodiments, the driven voltage may be held at a constant voltage such as, e.g., 2.2 V. In embodiments, the driven voltage can be controlled by device state. For example, while in shelf/storage mode, the device may be configured to either float case or drive to positive voltage such as shorting to the positive battery terminal. When entering an active mode such as sensing, the IMD can be configured to drive the case to a regulated voltage. According to other embodiments, the driven voltage can be controlled to match the battery discharge state. For example, the case may be driven to 2.5 V early in the cell state but then gradually reduced to 2.2 V as the battery is discharged and the average unloaded battery voltage decreases. This may have the advantage of keeping the driven voltage high to maintain a small voltage difference between the case and the battery anode while protecting against regulation issues as the battery voltage decreases.

In embodiments, the drive circuit may change operating mode based on device activity such as using a high-power mode when significant battery ripple is expected due to device activity. This may facilitate minimizing the energy consumed by the drive circuit over the life of the device. In embodiments, the case drive may be suspended during device activities that require driving the case to a different voltage or sensing case currents or voltages. For example, the case drive may be disconnected (tri-stated) when device therapy operation such as a pace pulse or impedance measurement current pulse is being driven through the case. In other words, embodiments include releasing the drive to the can for short periods of time when not sensing.

For example, in embodiments, the device may be configured to drive a voltage onto the case only during a certain period of the life of the device. In embodiments, noise is much more significant near a battery's end of life, as internal resistance of the battery changes as a function of depth of discharge. Thus, near the end of the battery's life, the case may be driven with a regulated voltage. In contrast, for example, in a storage mode before the device is implanted and active, the sensing circuit is off, and, thus, the presence of ripple is not an issue. Thus, in embodiments, while in the storage mode, the device may be shorted to the positive (as in a case-positive design), or let it float to the positive, which would mitigate the electrochemical issues. Once the device enters and active state in which it is sensing, the can may be configured in a case-driven design or a case-negative design.

For example, in embodiments, rather than implementing a case-driven design, the IMD may be configured to be shorted to positive or floated to positive during the storage mode, and placed in a case-negative design upon activation and/or implantation. This mode of operation may facilitate reducing the time and temperature exposure to limit the total electrochemical reaction that occurs. It also may facilitate reducing the amount of electrochemical reaction that occurs (by limiting both time and temperature exposure to a fully charged battery) while still having a simple drive circuit and reducing case ripple voltage while sensing.

The illustrative circuitry 500 shown in FIG. 5 is not intended to suggest any limitation as to the scope of use or functionality of embodiments of the subject matter disclosed throughout this disclosure. Neither should the illustrative circuitry 500 be interpreted as having any dependency or requirement related to any single component, feature, or combination of components or features illustrated in FIG. 5. For example, in embodiments, the illustrative circuitry 500 may include different and/or additional components and/or features. Any number of other components, features, or combinations of components or features can be integrated with the illustrative circuitry 500 depicted in FIG. 5, all of which are considered to be within the ambit of this disclosure. Additionally, any one or more of the components and/or features depicted in FIG. 5 can be, in embodiments, integrated with various ones of the other components and/or features depicted therein (and/or components and/or features not illustrated).

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. That is, for example, embodiments may include one or more filters and/or other components that facilitate interpreting sensed physiological signals in the presence of some interference caused by having an energy supply current sharing a portion of the physical sense pathway. Accordingly, the scope of the disclosed subject matter is intended to embrace all such alternatives, modifications, and variations as fall within the scope of the claims, together with all equivalents thereof.

We claim:

1. A medical device comprising:
   a case, wherein at least a portion of the case functions as a first electrode;
   a second electrode disposed in a header, which is coupled to the case;
   a core assembly, the core assembly comprising operational circuitry enclosed within a core assembly housing, wherein the case comprises the core assembly housing; and
   a battery assembly, the battery assembly comprising a battery enclosed within a battery housing, the battery including a positive terminal and a negative terminal,
   wherein the case is shorted to the positive terminal,
   wherein the case further comprises the battery housing,
   wherein a capacitor is electrically coupled between the negative terminal and the case,
   wherein the operational circuitry is configured to drive a voltage onto the case.

2. The medical device of claim 1, wherein the voltage regulator is configured to produce the voltage by reducing a power supply voltage provided by the battery.

3. The medical device of claim 1, further comprising a charge pump configured to facilitate increasing the voltage to a voltage level greater than a power supply voltage level provided by the battery.

4. The medical device of claim 1, wherein the voltage regulator is configured to provide a power supply to an input component.

5. The medical device of claim 1, further comprising an additional voltage regulator, wherein the additional voltage regulator is configured to provide a power supply to an input component.

6. A medical device comprising:
   a case, wherein at least a portion of the case functions as a first electrode configured to sense a physiological parameter;
   a second electrode disposed in a header, which is coupled to the case, the second electrode is configured to sense the physiological parameter;
   a core assembly comprising operational circuitry enclosed within a core assembly housing, wherein the case comprises the core assembly housing; and
   a battery assembly comprising a battery enclosed within a battery housing, the battery including a positive battery terminal and a negative battery terminal,
   wherein the case further comprises the battery housing and wherein the case is shorted to the positive battery terminal,
   wherein a capacitor is electrically coupled between the negative battery terminal and the case,
   wherein the operational circuitry is configured to drive a voltage onto the case.

7. The medical device of claim 6, the operational circuitry comprising a voltage regulator disposed between the battery and the case, the voltage regulator configured to drive the voltage onto the case.

8. The medical device of claim 7, wherein the voltage regulator is configured to produce the voltage by reducing a power supply voltage provided by the battery.

9. The medical device of claim 7, wherein the voltage regulator is configured to provide a power supply to an input component.

10. The medical device of claim 7, further comprising an additional voltage regulator configured to provide a power supply to an input component.

11. The medical device of claim 7, wherein the operational circuitry is configured to drive the voltage at a level that is selected based on a battery discharge state.

12. The medical device of claim 6, further comprising a charge pump configured to facilitate increasing the voltage to a voltage level greater than a power supply voltage level provided by the battery.

13. The medical device of claim 6, wherein the operational circuitry is configured to drive the voltage onto the case in response to determining that the medical device is in an active mode.

14. The medical device of claim 6, wherein the voltage is at a level of 6-2.5 volts.

15. A method of manufacturing a medical device, the method comprising:
   providing a case, wherein at least a portion of the case functions as a first electrode;
   coupling a header to the case;
   disposing a second electrode in the header;
   providing a core assembly, the core assembly comprising operational circuitry enclosed within a core assembly housing, wherein the case comprises the core assembly housing;
   coupling a battery assembly to the core assembly, the battery assembly comprising a battery enclosed within a battery housing, the battery including a positive terminal and a negative terminal; and
   shorting the case to the positive terminal;
   wherein the case further comprises the battery housing,
   wherein a capacitor is electrically coupled between the negative terminal and the case,
   wherein the operational circuitry is configured to drive a voltage onto the case.

16. The method of claim 15, further comprising providing a voltage regulator disposed between the battery and the case, the voltage regulator configured to drive the voltage onto the case.

17. The method of claim 16, wherein the voltage regulator is configured to produce the voltage by reducing a power supply voltage provided by the battery.

18. The method of claim 15, wherein the voltage regulator is configured to provide a power supply to an input component.

19. The method of claim 16, further comprising providing an additional voltage regulator configured to provide a power supply to an input component.

20. The method of claim 15, wherein the operational circuitry is configured to drive the voltage onto the case in response to determining that the medical device is in an active mode.

\* \* \* \* \*